US010629105B2

United States Patent
Perreault et al.

(10) Patent No.: US 10,629,105 B2
(45) Date of Patent: Apr. 21, 2020

(54) NEAR-EYE DISPLAY WITH FRAME RENDERING BASED ON REFLECTED WAVEFRONT ANALYSIS FOR EYE CHARACTERIZATION

(71) Applicant: Google LLC, Mountain View, CA (US)

(72) Inventors: John D. Perreault, Mountain View, CA (US); Patrick Llull, San Jose, CA (US)

(73) Assignee: GOOGLE LLC, Mountain View, CA (US)

( * ) Notice: Subject to any disclaimer, the term of this patent is extended or adjusted under 35 U.S.C. 154(b) by 63 days.

(21) Appl. No.: 15/917,375

(22) Filed: Mar. 9, 2018

(65) Prior Publication Data
US 2018/0366045 A1 Dec. 20, 2018

Related U.S. Application Data

(60) Provisional application No. 62/520,295, filed on Jun. 15, 2017.

(51) Int. Cl.
*G09G 3/00* (2006.01)
*H04N 13/344* (2018.01)
(Continued)

(52) U.S. Cl.
CPC ............... *G09G 3/001* (2013.01); *A61B 3/10* (2013.01); *A61B 3/1015* (2013.01); *H04N 5/332* (2013.01);
(Continued)

(58) Field of Classification Search
CPC .. H04N 13/383; H04N 13/332; H04N 13/344; G09G 3/001
See application file for complete search history.

(56) References Cited

U.S. PATENT DOCUMENTS 8,487,838 B2   7/2013  Lewis et al.
9,841,537 B2  12/2017  Luebke et al.
(Continued)

FOREIGN PATENT DOCUMENTS

TW    201643506 A   12/2016
WO    20040107301   12/2004

OTHER PUBLICATIONS

Taiwanese Office Action dated Nov. 28, 2018 for corresponding TW Application No. 107109327, 3 pages.
(Continued)

*Primary Examiner* — Kent W Chang
*Assistant Examiner* — Chayce R Bibbee

(57) ABSTRACT

A near-eye display system includes an array of lenslets overlying a display panel. The display panel includes an array of light projecting elements, each light projecting element being coaxial with an axis of a corresponding lenslet. The display panel further includes an array of light detecting elements and an array of sub-pixel elements. The system further includes a control component configured to activate the array of light projecting elements to project a pattern of light spots toward an eye of the user and to control the array of light detecting elements to capture an image representing a reflection of the projected pattern of light spots from the eye. The system also includes an analysis component to determine displacements between expected positions and actual positions of at least a subset of light spots in the captured image, and to characterize the eye based on the displacements.

20 Claims, 5 Drawing Sheets

(51) Int. Cl.

| | | |
|---|---|---|
| H04N 13/383 | (2018.01) | |
| H04N 13/398 | (2018.01) | |
| H04N 5/369 | (2011.01) | |
| A61B 3/10 | (2006.01) | |
| H04N 5/33 | (2006.01) | |
| H01L 27/146 | (2006.01) | |

(52) U.S. Cl.
CPC ......... *H04N 5/3696* (2013.01); *H04N 13/344* (2018.05); *H04N 13/383* (2018.05); *H04N 13/398* (2018.05); *G09G 2354/00* (2013.01); *H01L 27/14645* (2013.01)

(56) References Cited

U.S. PATENT DOCUMENTS

| | | |
|---|---|---|
| 2002/0181115 A1 | 12/2002 | Massof et al. |
| 2004/0207635 A1 | 10/2004 | Miller et al. |
| 2006/0256219 A1 | 11/2006 | Schroderus |
| 2007/0216867 A1 | 9/2007 | Campbell et al. |
| 2012/0068916 A1 | 3/2012 | Tsubata |
| 2012/0274734 A1 | 11/2012 | Byers |
| 2013/0050432 A1 | 2/2013 | Perez et al. |
| 2013/0207887 A1 | 8/2013 | Raffle et al. |
| 2013/0285885 A1 | 10/2013 | Nowatzyk et al. |
| 2014/0145939 A1 | 5/2014 | Herold et al. |
| 2014/0362110 A1 | 12/2014 | Stafford |
| 2015/0015814 A1 | 1/2015 | Qin |
| 2015/0185475 A1 | 7/2015 | Saarikko et al. |
| 2015/0312560 A1 | 10/2015 | Deering |
| 2016/0091720 A1 | 3/2016 | Stafford et al. |
| 2016/0209647 A1 | 7/2016 | Fursich |
| 2016/0313558 A1 | 10/2016 | Gutierrez |
| 2016/0320620 A1 | 11/2016 | Maimone |
| 2016/0379606 A1 | 12/2016 | Kollin et al. |
| 2017/0038590 A1 | 2/2017 | Jepsen |
| 2017/0038834 A1 | 2/2017 | Wilson et al. |
| 2017/0205877 A1 | 7/2017 | Qin |
| 2017/0269367 A1 | 9/2017 | Qin |

OTHER PUBLICATIONS

Written Opinion of the International Preliminary Examining Auhority dated Jan. 18, 2019 for corresponding International Application No. PCT/US2018/017590, 5 pages.
Final Office Action dated Jan. 15, 2019 for U.S. Appl. No. 15/595,147, 17 pages.
English translation of Taiwanese Office Action dated Jan. 28, 2019 for corresponding TW Application No. 107105857, 13 pages.
International Search Report and Written Opinion dated May 18, 2018 for PCT Application No. PCT/US2018/022440, 13 pages.
International Search Report and Written Opinion dated May 7, 2018 for PCT Application No. PCT/US2018/017590, 20 pages.
Lanman, et al., "Near-Eye light field displays," ACM Transactions on Graphics (TOG), ACM, US, vol. 32, No. 6, Nov. 1, 2013, XP0508033862, ISSN:07030-0301, DOI:10.1145/2508363.2508366, 10 pages.
Non-Final Office Action dated Jun. 6, 2019 for U.S. Appl. No. 15/595,147, 19 pages.
Boston Micromachines Corporation, "Adaptive Optics 101: Overview, Tech Review & Applications Introduction and Motivation," Shaping Light Blog, Technical whitepaper; accessed Sep. 12, 2018 <<https://blog.bostonmicromachines.com/hs-fs/hub/1703/.../ao_101_white_paper.pdf>>; 12 pages.
Pamplona, V. et al., "NETRA: Interactive Display for Estimating Refractive Errors and Focal Range," Proc. of SIGGRAPH Jan. 2010; Artcle No. 77; 8 pages.
Thibos, Larry N. "Principles of Hartmann-Shack Aberrometry," Journal of Refractive Surgery, vol. 16; Sep./Oct. 2000; 3 pages.
Wyant, J. et al. "Chapter 1: Basic Wavefront Aberration Theory for Optical Metrology," Applied Optice and Optical Engineering, vol. XI; Jan. 1992, ISBN 0-12-408611-X; 13 pages.
Non-Final Office Action dated Aug. 16, 2018 for U.S. Appl. No. 15/595,147, 15 pages.
International Preliminary Report on Patentability dated Sep. 13, 2018 for PCT/US18/022440, 6 pages.
Wikipedia, <https://en.wikipedia.org/wiki/Shack%E2%80%93Hartmann_wavefront_sensor>, Accessed Mar. 15, 2017, 2 pages.
Maimone, A., et al., "Pinlight Displays: Wide Field of View Augmented Reality Eyeglasses using Defocused Point Light Sources", ACM Trans. Graph., 33, 4, Article 89, Jul. 2014, 11 pages.
Zhang, S., "The Obscure Neuroscience Problem That's Plaguing VR", <https://www.wired.com/2015/08/obscure-neuroscience-problem-thats-plaguing-vr/>, Accessed May 15, 2017, 5 pages.
Patney, A., et al., "Towards Foveated REndering for Gaze-Tracked Virtual Reality", NVIDIA, ACM Trans. Graph., vol. 35, No. 6, Article 179, Nov. 2016, 12 pages.
Pfeiffer, T., et al, "Evaluation of Binocular Eye Trackers and Algorithms for 3D Gaze Interaction in Virtual Reality Environments", Journal of Virtual Reality and Broadcasting, No. 16, May 2008, 13 pages.
U.S. Appl. No. 15/595,147, filed May 15, 2017, listing John D. Perreault, et al., as inventors, entitled Near-Eye Display With Extended Effective Eyebox Via Eye Tracking, 49 pages.
Notice of Allowance dated Nov. 6, 2019 for U.S. Appl. No. 15/595,147, 12 pages.

NEAR-EYE DISPLAY WITH FRAME RENDERING BASED ON REFLECTED WAVEFRONT ANALYSIS FOR EYE CHARACTERIZATION

CROSS-REFERENCE TO RELATED APPLICATIONS

The present disclosure claims priority to U.S. Provisional Patent Application Ser. No. 62/520,295, entitled "Near-Eye Display with Frame Rendering Based on Reflected Wavefront Analysis for Eye Characterization" and filed on Jun. 15, 2017, the entirety of which is incorporated by reference herein.

BACKGROUND

Field of the Disclosure

The present disclosure relates generally to near-eye displays and, more particularly, to frame rendering for computational near-eye displays.

Description of the Related Art

Head-mounted displays (HMDs) and other near-eye display systems can utilize a near-eye lightfield display or other computational display to provide effective display of three-dimensional (3D) graphics. Generally, the near-eye lightfield display employs one or more display panels and an array of lenslets, pinholes, or other optic features that overlie the one or more display panels. A rendering system renders an array of elemental images, with each elemental image representing an image or view of an object or scene from a corresponding perspective or virtual camera position.

Generally, each array of elemental images is rendered with reference to a particular focal plane, and is rendered based on an assumption that the user's eye is free of substantial aberrations. However, if the user's eye is subject to refractive errors or other aberrations, the displayed imagery may appear blurry or distorted. To avoid such issues, the near-eye display device could be designed to permit the user to wear corrective eyeglasses, but the resulting form factor typically is impracticable for weight, inertial, and size reasons. Similarly, if the current accommodation state of the user's eye is not consistent with the focal plane for which the array of elemental images is rendered results in inconsistent depth cues that can result in cognitive fatigue for the user and thus detract from the user's experience.

BRIEF DESCRIPTION OF THE DRAWINGS

The present disclosure may be better understood, and its numerous features and advantages made apparent to those skilled in the art by referencing the accompanying drawings. The use of the same reference symbols in different drawings indicates similar or identical items.

DETAILED DESCRIPTION

Figure 1:
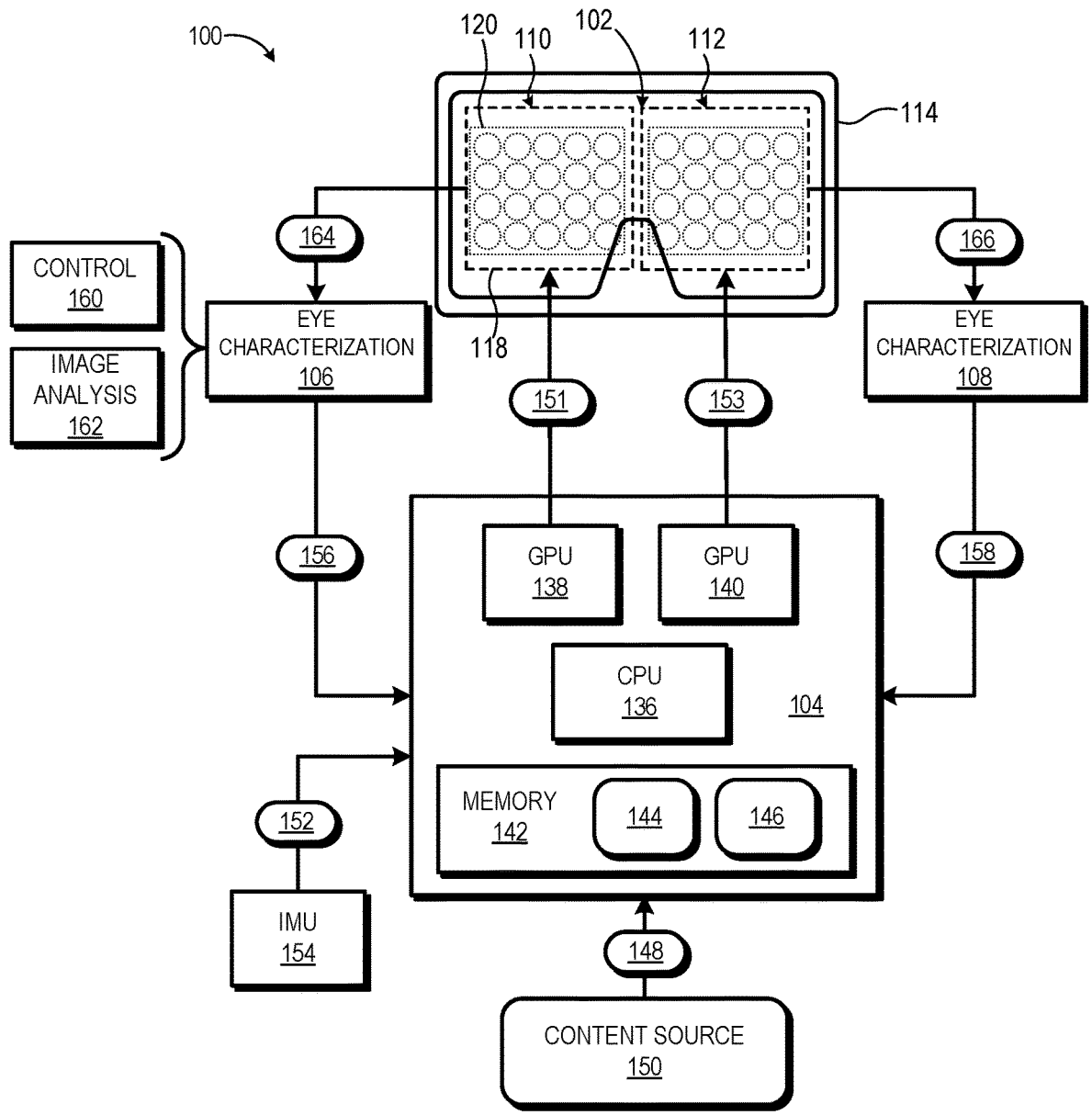
FIG. 1 is a diagram illustrating a near-eye display system employing lightfield frame rendering based on eye characterization via wavefront distortion estimation in accordance with some embodiments.

FIGS. 1-5 illustrate example systems and techniques for improved image rendering in a near-eye display system based on characterization of a user's eye using wavefront distortion estimation. In at least one embodiment, the near-eye display system employs a computational display composed of one or more display panels to display near-eye lightfield frames of imagery to a user so as to provide the user with an immersive virtual reality (VR) or augmented reality (AR) experience. Each near-eye lightfield frame is composed of an array of elemental images, with each elemental image representing a view of an object or scene from a different corresponding viewpoint. An array of lenslets overlies each display panel and operates to present the array of elemental images to the user as a single autostereoscopic image.

In addition to displaying AR or VR video imagery to the user, the display panel also facilitates characterization of one or both of the user's eyes via a wavefront distortion estimation process. To this end, in at least one embodiment the display panel incorporates both an array of light projecting elements (infrared (IR) light projecting diodes, for example) to transmit a pattern of light spots toward the eye through the lenslet array and an array of light detecting elements (photodiodes, for example) to capture a reflection of the light spot pattern from the structures of the eye as a pattern reflection image.

In an eye without aberrations, the wavefront exiting the eye as a result of reflection of the light spot pattern would be completely flat and thus the wavefront would hit the lenslets of the lenslet array straight on. As a result, the pattern of light spots in the captured image of the reflected light spot pattern would match the pattern of light spots in the light spot pattern projected by the array of light projecting elements. That is, in a perfect eye, the actual location of a light spot in the captured reflected pattern would coincide with an expected location of the corresponding light spot assuming a perfectly flat wavefront. In contrast, imperfections in one or more of the cornea, retina, or shape of the eye or other eye aberrations distort the wavefront exiting the eye. These distortions in the wavefront in turn cause corresponding rays of the wavefront to strike a corresponding lenslet of the lenslet array at an angle, which in turn causes the actual location of the corresponding reflected light spot to shift from the corresponding expected location in the reflected pattern image.

The magnitude of the displacement of the actual location from the expected location of a reflected light spot is proportional to the slope of the location region of the wavefront at the corresponding lenslet, while the angle of the displacement is based on the direction or angle of this slope. In view of these principles, the near-eye display system can determine the shape of the wavefront from the actual/expected location displacements of the reflected light spots. The near-eye display system then may use some or all of the identified wavefront distortions (that is, deviations of the shape of the wavefront from a flat wavefront) to characterize the user's eye. This characterization of the user's eye can include, for example, identification of aberrations present in the user's eye, identification of the current accommodation state of the user's eye, and the like.

The near-eye display system utilizes the characterization of the eye to control one or more aspects of the rendering process for a sequence of lightfield frames to be displayed at the display panel. To illustrate, in some embodiments, the near-eye display system controls the rendering of a lightfield frame to compensate for the detected aberrations in the user's eye. In such a manner, the near-eye display system may provide prescriptive correction for various imperfections of the eye that otherwise would require the user to wear eyeglasses, contact lenses, or other corrective lenses for corrective purposes, and thus eliminate the user's need to wear such corrective lenses while utilizing the near-eye display system. As the near-eye display system would thus no longer have need to facilitate the user's wearing of eyeglasses during use, the near-eye display system can implement a configuration that places the lenslet array and display panel closer to the user's eyes, and thus resulting in a smaller and lighter form factor. As another example, in some embodiments the near-eye display system renders lightfield frames on the basis of an specified focal plane, and the near-eye display system may use the characterization of the eye to determine the eye's current accommodation state, and from this current accommodation state select the appropriate focal plane for rendering of the lightfield frames so that the user is presented with depth cues in the lightfield frames that are consistent with the current accommodation state, and thus enabling an effectively immersive experience for the user.

FIG. 1 illustrates a near-eye display system 100 incorporating eye characterization-based graphics rendering in accordance with at least one embodiment. In the depicted example, the near-eye display system 100 includes a computational display sub-system 102, a rendering component 104, and one or more eye characterization components, such as one or both of an eye characterization component 106 for characterizing a user's left eye and an eye characterization component 108 for characterizing the user's right eye. The computational display sub-system 102 includes a left-eye display 110 and a right-eye display 112 mounted in an apparatus 114 (e.g., goggles, glasses, etc.) that places the displays 110, 112 in front of the left and right eyes, respectively, of the user.

Figure 2:
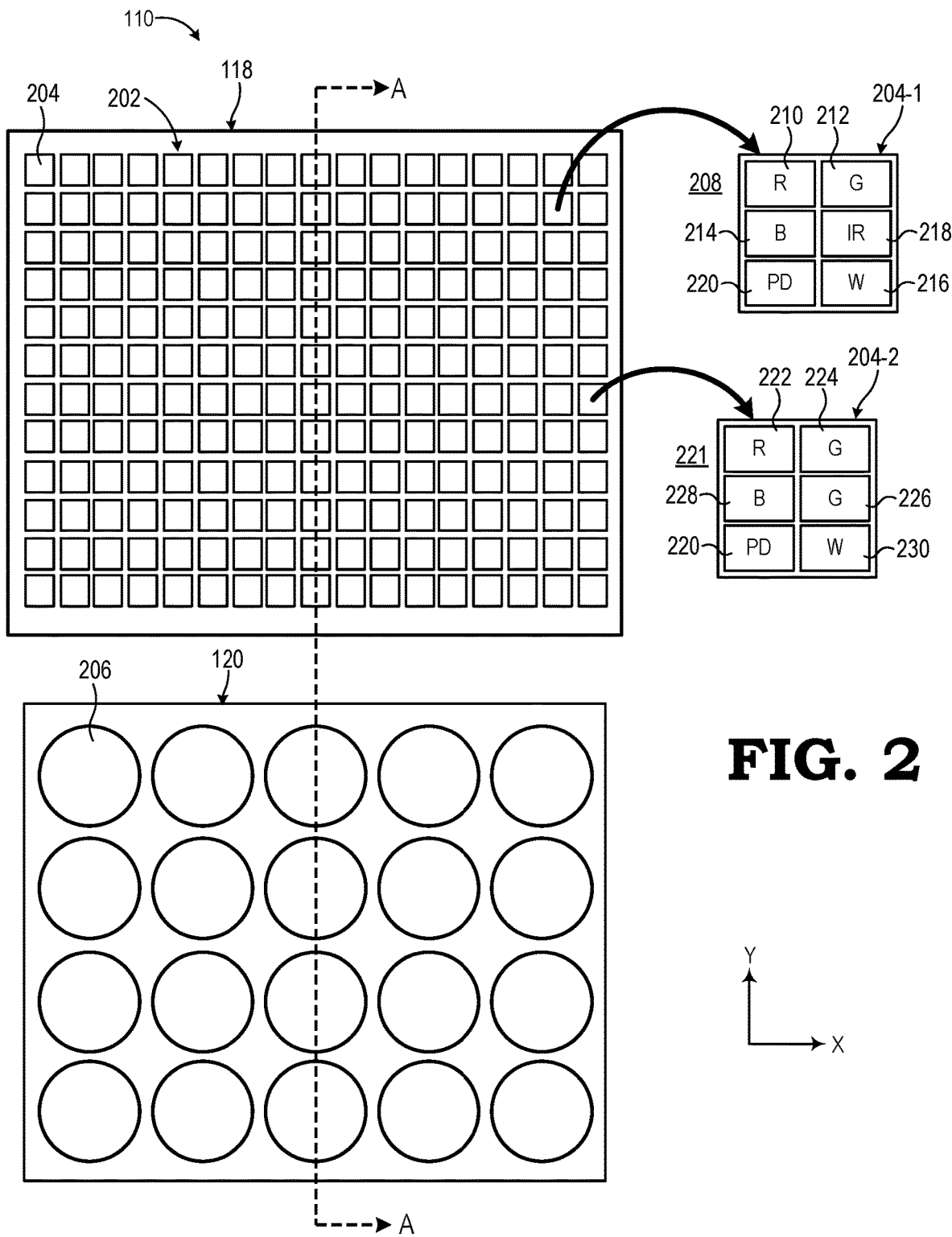
FIG. 2 is a diagram illustrating a display panel and overlying lenslet array of the near-eye display system of FIG. 1 in greater detail in accordance with some embodiments.

Referring briefly to FIG. 2, an expanded view of the display 110 is depicted in accordance with at least one embodiment. The display 112 is similarly configured. As shown, the display 110 includes at least one display panel 118 to display a sequence or succession of near-eye lightfield frames (hereinafter, "lightfield frame" for ease of reference), each of which comprises an array of elemental images. For ease of reference, an array of elemental images may also be referred to herein as a lightfield frame. The display 110 further includes an array 120 of lenslets 206 (also commonly referred to as "microlenses") overlying the display panel 118. Typically, the number of lenslets 206 in the lenslet array 120 is equal to the number of elemental images in a lightfield frame, but in other implementations the number of lenslets 206 may be fewer or greater than the number of elemental images. Note that while the example of FIG. 1 illustrates a 5×4 array 120 of lenslets 206 for ease of illustration, in a typical implementation the number of elemental images in a lightfield frame and the number of lenslets 206 in the lenslet array 120 typically is much higher. Further, in some embodiments, a separate display panel 118 is implemented for each of the displays 110, 112, whereas in other embodiments the left-eye display 110 and the right-eye display 112 share a single display panel 118, with the left half of the display panel 118 used for the left-eye display 110 and the right half of the display panel 118 used for the right-eye display 112.

As shown in FIG. 2, the display panel 118 implements an array 202 of display elements 204 (e.g., "pixels"), with each display element 204 comprising one or more color sub-pixels, such as a set of red, green, blue, and white sub-pixels which are controlled in intensity so that their combined light output is perceived by the eye as a single "pixel" of a particular color. In this manner, the rendering component 104 can control the array 202 to display a sequence of lightfield frames that represent imagery of a scene.

Further, as described in greater detail herein, the near-eye display system 100 projects a light spot pattern to an eye of the user through the lenslet array 120 and captures an image of the reflection of the light spot pattern through the lenslet array 120 so as to analyze the eye for detection of aberrations, estimation of accommodation state, or otherwise characterize the eye. In at least one embodiment, the near-eye display system 100 uses the display panel 118 both to project the light spot pattern and to capture an image of the resulting reflected light spot pattern. To this end, the display panel 118 also incorporates a set of light-projecting elements that, when activated, project a light spot pattern toward the user's eye via the lenslet array 120 and a set of light-detecting elements that, when activated, together capture an image that represents the reflection of the projected light spot pattern from the user's eye through the lenslet array 120.

In at least one embodiment, the set of light-projecting elements and set of light-detecting elements are incorporated in the array 202 of display elements 204, such that a subset of the display elements 204 incorporate a light-projecting element of the set of light-projecting elements and a subset of the display elements 204 incorporate a light-detecting element of the set of light-detecting elements. For example, a subset of the display elements 204 of the array 202 may be implemented as display elements 204-1, which as shown by enlarged view 208 includes a set of color sub-pixels, such as a red (R) sub-pixel 210, a green (G) sub-pixel 212, a blue (B) sub-pixel 214, and a white (W) sub-pixel 216. The display elements 204-1 of this subset further include an infrared (IR) sub-pixel 218 (one embodiment of a light-projecting element) that operates to emit IR light as part of the projected light spot pattern. The IR sub-pixel 218 is implemented as, for example, an IR-projecting vertical-cavity surface-projecting laser (VECSEL), an IR light projecting diode (LED), and the like. Some or all of the display elements 204-1 further can include a IR-detecting photodiode (PD) 220 (one embodiment of a light-detecting element) that operates to detect IR light incident on the display panel 118, and particularly a reflection of the IR light projected by the IR sub-pixels 218 of the display elements 204-1 in a corresponding light spot pattern. Further, another subset of the display elements 204 of the array 202 may be implemented as display elements 204-2, which as shown by enlarged view 221 include a set of color sub-pixels, such as red sub-pixel 222, green sub-pixels 224, 226, blue sub-pixel 228, white sub-pixel 230, and a IR photodiode 220 (as one of the light-detecting elements). Note that the arrangements and types of sub-pixels in the display elements 204-1 and 204-2 are examples only, and other arrangements, organizations, and combinations of sub-pixels may be implemented.

The display elements 204-1 with IR projecting capabilities are dispersed throughout the array 202 in a specified pattern so that when the IR sub-pixels 218 of the display elements 204-1 are activated together, the resulting projected IR light is projected in a pattern of light spots (e.g., a rectangular or other polygonal grid of regularly-spaced spots), an example of which is described below with reference to FIG. 5. Further, as described below, the display elements 204-1 are arranged to be coaxial with corresponding lenslets 206 of the lenslet array 120 so that the projected IR light strikes the corresponding lenslet straight on. The display elements 204-1 and 204-2 with IR detecting capabilities are dispersed throughout the array 202 in a manner that permits the photodiodes 220 of these display elements to be activated together to capture the IR light incident on the areas of the display panel 118 corresponding to the location of the photodiodes 220, and as this incident IR light at the time of capture is primarily composed of a reflection of the projected IR light spot pattern off of the user's eye, the photodiodes 220 together operate to capture an image of this reflected IR light spot pattern. As such, this image is referred to herein as the "reflected spot pattern image," an example of which is described below with reference to FIG. 5.

Referring back to FIG. 1, the rendering component 104 includes a set of one or more processors, such as the illustrated central processing unit (CPU) 136 and graphics processing units (GPUs) 138, 140 and one or more storage components, such as system memory 142, to store software programs or other executable instructions that are accessed and executed by the processors 136, 138, 140 so as to manipulate the one or more of the processors 136, 138, 140 to perform various tasks as described herein. Such software programs include, for example, a rendering program 144 comprising executable instructions for a lightfield frame rendering process, as described below, as well as an eye characterization program 146 comprising executable instructions for characterizing one or both of the user's eyes based on wavefront distortion analysis, as also described below.

In operation, the rendering component 104 receives rendering information 148 from a local or remote content source 150, where the rendering information 148 represents graphics data, video data, or other data representative of an object or scene that is the subject of imagery to be rendered and displayed at the display sub-system 102. Executing the rendering program 144, the CPU 136 uses the rendering information 148 to send drawing instructions to the GPUs 138, 140, which in turn utilize the drawing instructions to render, in parallel, a series of lightfield frames 151 for display at the left-eye display 110 and a series of lightfield frames 153 for display at the right-eye display 112 using any of a variety of well-known VR/AR computational/lightfield rendering processes. As part of this rendering process, the CPU 136 may receive pose information 152 from an inertial management unit (IMU) 154, whereby the pose information 152 is representative of a pose of the display sub-system 102 and control the rendering of one or more pairs of lightfield frames 151, 153 to reflect the viewpoint of the object or scene from the pose.

In parallel, the eye characterization components 106, 108 operate to dynamically characterize the user's eyes using a wavefront distortion analysis process described herein, and provide the determined eye characterizations to the rendering component 104 as eye characterization information 156, 158 for the left eye and right eye, respectively. The characterization process includes projecting an IR light spot pattern from the display panel 118 to the user's eye through the lenslet array 120 and then capturing an image of the reflected light pattern via the display panel, determining the displacements between where the reflected light spots are expected to be in the captured image and where the reflected light spots actually are located in the captured image. These displacements represent distortions in the wavefront representing the reflection of the light spot pattern from the user's eye, and thus may be used to identify refractive aberrations, a current accommodation state, or other characteristics of the eye, which are represented in the corresponding one of the eye characterization information 156, 158.

To facilitate this operation, the eye characterization component 106 implements a control component 160 and an image analysis component 162. The control component 160 operates to trigger activation of the set of light projecting elements of the display panel 118 so as to project the light spot pattern and to trigger activation of the light detecting elements of the display panel 118 to capture a reflected spot pattern image 164 representing the resulting reflection of the projected light spot pattern. The image analysis component 162 operates to analyze the spot pattern image 164 to characterize the left eye so as to generate the eye characterization information 156 for the rendering component 104. The eye characterization component 108 is similarly configured with a control component and an image analysis component to capture and analyze a reflected spot pattern image 166 for generating the eye characterization information 158 for the right eye. The control components and image analysis components may be implemented as hardware, programmable logic, a processor executing software, or a combination thereof. To illustrate, in one embodiment, the control component 160 is implemented at least partially in the hardware of a display controller (not shown) for the display panel 118, whereas the image analysis component 162 is implemented by one or more of the processors 136, 138, 140 executing a corresponding set of instructions of the eye characterization program 146.

As described in detail below, the rendering component 104 use one or both of eye characterization information 156, 158 from one or both of the eye characterization components 106, 108 to control various aspects of the lightfield frame rendering process in generating the sequences of lightfield frames 151, 153. To illustrate, the eye characterization information 156 may include information identifying one or more aberrations in the left eye, and thus the CPU 136 may control the operation of the GPU 138 so as to adjust the rendering of the lightfield frames 151 to compensate for these aberrations, thereby allowing the user to forgo wearing corrective lenses while using the near-eye display system 100. As another example, the eye characterization information 156 may include information identifying a current accommodation state of the eye, and the rendering component 104 may use this to render lightfield frames 151 for a focal plane that is consistent with the current accommodation state.

Figure 3:
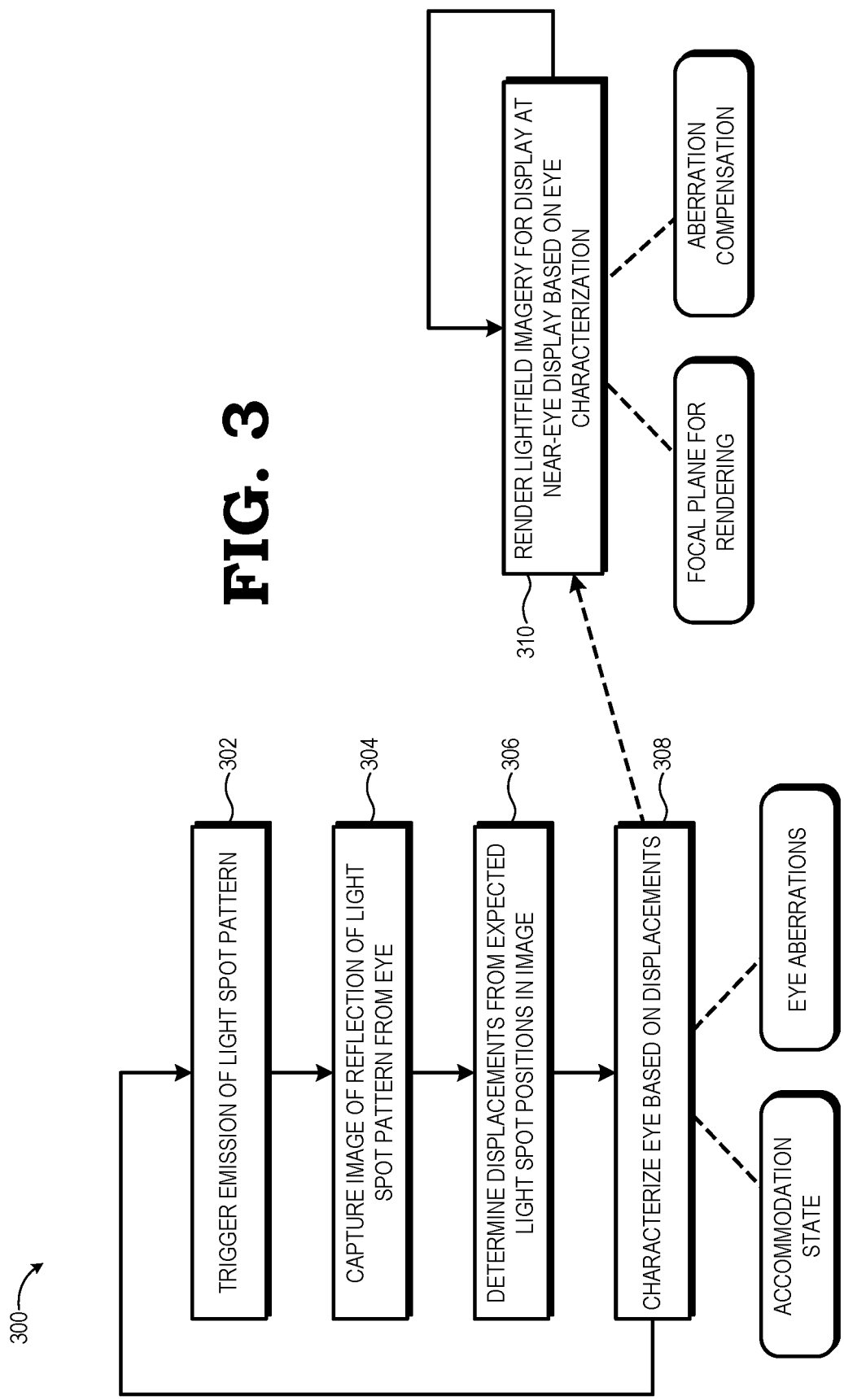
FIG. 3 is a flow diagram illustrating a method for characterizing a user's eye based on wavefront distortion estimation and controlling an imagery rendering process based on the eye characterization in accordance with some embodiments.

FIG. 3 illustrates an example method 300 of operation of the near-eye display system 100 for characterizing the user's eyes and controlling one or more rendering operations accordingly. For ease of illustration, method 300 is described with reference to FIG. 4, which depicts cross-section views 400, 402 of the display panel 118, the overlying lenslet array 120, and a facing eye 404 of the user along a cut line A-A (FIG. 2), and with reference to FIG. 5, which depicts an example of the reflected spot pattern image 164. Moreover, the method 300 is described with particular reference to the operation of the near-eye display system 100 with respect to the left eye (eye 404), including the eye characterization component 106. However, this same method can be applied to the operation of the near-eye display system 100 for the right eye with the eye characterization component 108.

As illustrated by FIG. 3, the method 300 includes two processes that are performed in parallel: an eye characterization process represented by blocks 302, 304, 306, 308, and a lightfield frame rendering process represented by blocks 310. Turning first to the eye characterization process, at block 302 the control component 160 controls the display panel 118 to trigger photodiodes 220 of the display panel 118 (including the photodiodes 220-1, 220-2, 220-3, 220-4 illustrated in FIG. 4) so as to emit IR light in a light spot pattern directed toward the eye 404 via the lenslet array 120, as illustrated by cross-section view 400 of FIG. 4. Concurrent with triggering the emission of the light spot pattern, at block 304 the control component 160 activates the photodiodes 220 of the display panel 118 (as a set of light detecting elements) to capture the reflected spot pattern image 164 representing the reflection of the projected light spot pattern off the eye 404 and focused on the display panel 118 via the lenslet array 120.

Figure 4:
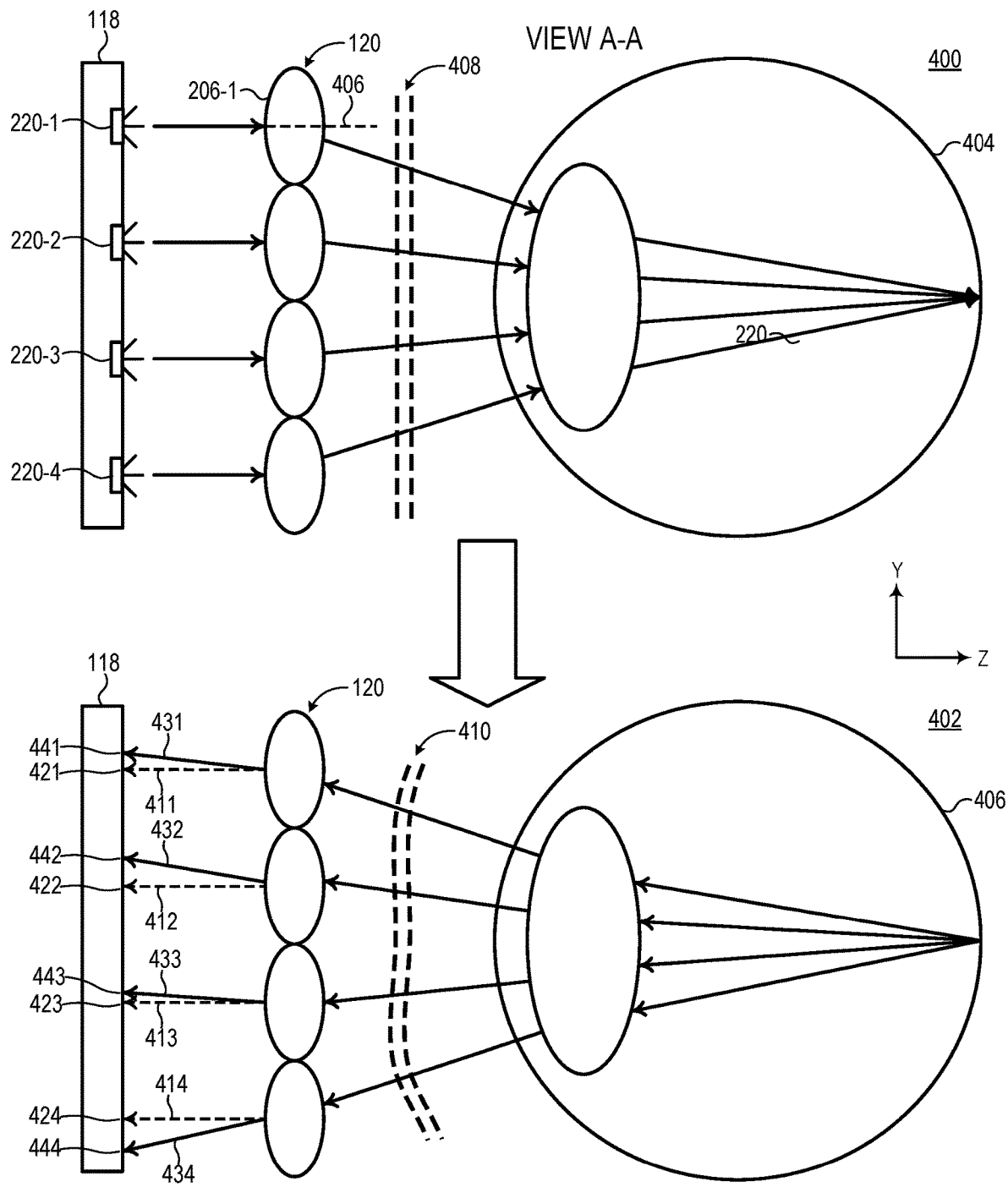
FIG. 4 is a diagram illustrating a cross-section view of the display panel and the overlying lenslet array during an eye characterization process in accordance with some embodiments.

As illustrated by cross-section view 400, each of the photodiodes 220 used for light spot pattern generation typically is substantially co-axial with the optical axis of a corresponding lenslet 206 (e.g., photodiode 220-1 is coaxial with the optical axis 406 of the lenslet 206-1 in FIG. 4) so that the IR light projected by the photodiode 220 strikes the corresponding lenslet 206 straight on, and thus is transmitted from the lenslet array 120 toward the eye 404 as a substantially flat wavefront 408 (that is, light spot pattern is transmitted toward the eye 404 without substantial distortion).

As illustrated by cross-section view 402, the light spot pattern so transmitted strikes the pupil, lens, cornea, retina, and other structures of the eye 404 and is reflected back toward the lenslet array 120 and display panel as a reflected light spot pattern represented by wavefront 410. In an ideal eye, the absence of aberrations would result in the reflected light spot pattern being clear of any distortions, and thus the wavefront 410 would be undistorted. In such a situation, an undistorted reflected wavefront incident on the lenslet array 120 would result in the light rays representing the spots within the reflected light pattern to strike the display panel 118 in expected locations. To illustrate, if the eye 404 were an idealized eye without aberrations, the reflected wavefront 410 would be undistorted and thus result in rays 411, 412, 413, 414 (representing corresponding spots in the reflected light spot pattern) striking the display panel 118 at expected locations 421, 422, 423, 424, respectively.

However, in a real eye, such as eye 404, aberrations in the eye result in localized distortions in the reflected light spot pattern; that is, the reflected wavefront 410 is distorted by aberrations in the eye 404. The local distortions in the reflected wavefront 410 cause the distorted regions of the wavefront 410 to strike corresponding lenslets 206 at an angle rather than straight on, and the resulting rays strike the display panel 118 at locations different from the expected locations. To illustrate, in cross-section view 402, the eye 404 has aberrations that distort the wavefront 410 such that actual rays 431, 432, 433, 434 transmitted by the lenslet array 120 strike the display panel 118 at actual locations 441, 442, 443, 444 that may differ from the expected location for the corresponding ray. As the lenslet array 120 is a pupil conjugate plane, the shape of the wavefront 410 represents the shape of the pupil of the eye 404, and the magnitude of the linear displacement between the actual location and expected location of a light spot in the captured reflected spot pattern image is proportional to the slope of the local region of the wavefront 410 that struck the corresponding lenslet 206, while the direction of the linear displacement represents the direction of the slope of the local region of the wavefront 410. The magnitude and direction of the slope of the local regions of the wavefront 410, in turn, represent characteristics of the eye 404, including any refractive aberrations present, as well as the current accommodation state of the eye 404.

Figure 5:
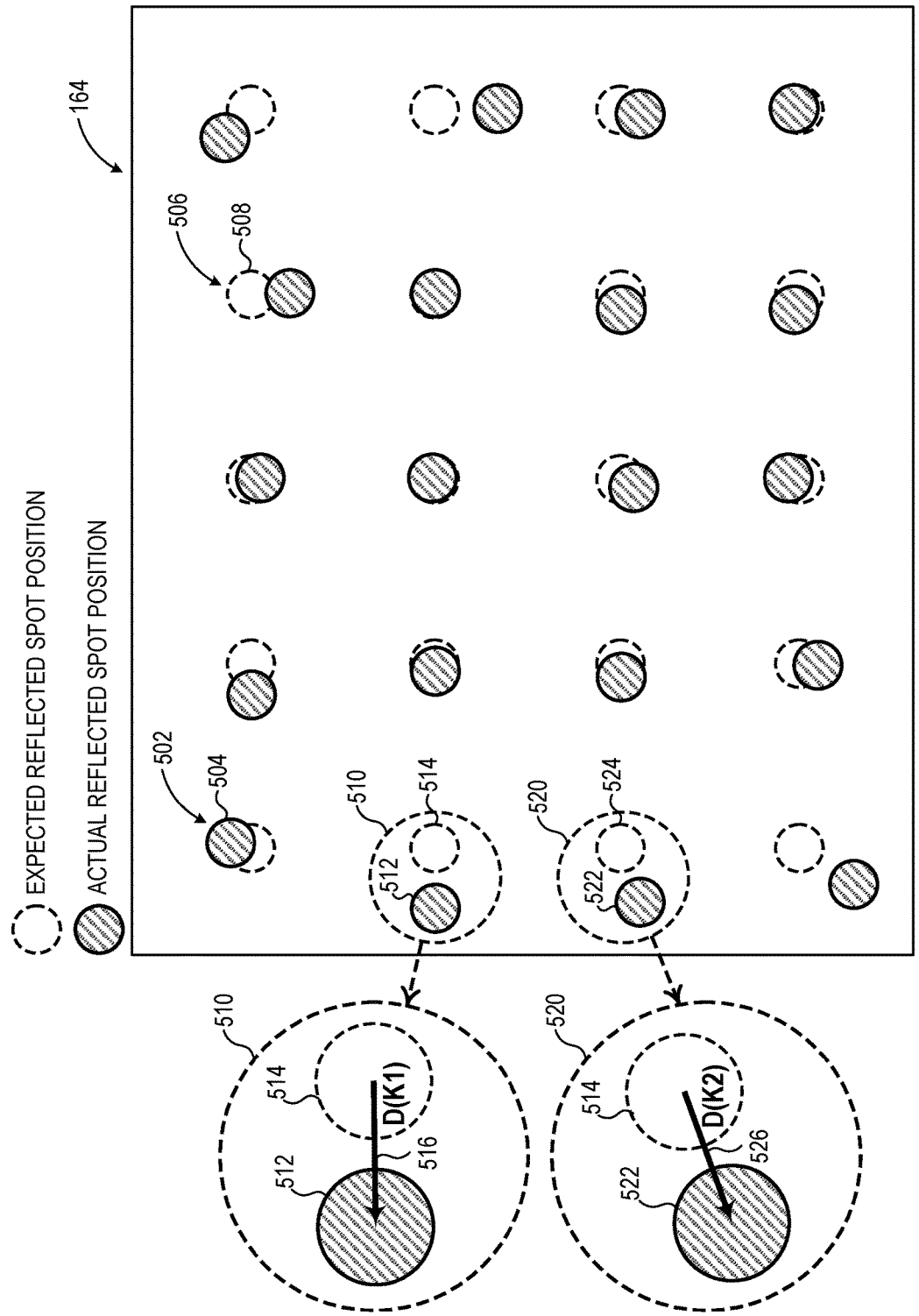
FIG. 5 is a diagram illustrating an image capturing a reflection of a light spot pattern projected by the display panel of FIG. 2 from an eye of a user in accordance with some embodiments.

To illustrate, FIG. 5 illustrates an example of the reflected spot pattern image 164. As shown, the reflected spot pattern image 164 comprises an array 502 of spots (e.g., spot 504), each spot reflecting an actual position of a detected light spot reflected from the eye 404 during transmission of the light spot pattern at block 302. For comparative purposes, FIG. 5 also includes an array 506 of expected positions (e.g., expected position 508) of the spots in the absence of any aberrations in the eye 404 (that is, if the eye 404 were an ideal eye). As illustrated, assuming the array of light projecting elements of the display panel 118 are arranged so as to project a pattern of light spots in a regular, fixed-spacing pattern, the array 506 of expected positions likewise will represent a regular, fixed-spacing pattern. However, as the user's eye 404 is unlikely to be an ideal eye, aberrations in the user's eye 404 will distort the reflected wavefront 410, and thus cause the actual locations of at least some of spots in the captured spot pattern image 164 to be displaced from their expected locations. To illustrate with reference to expanded view 510, an aberration in the eye 404 caused a local distortion in the wavefront 410, which in turn resulted in a corresponding reflected spot registering at an actual location 512 that is displaced from its expected location 514 by a displacement 516 (also denoted as displacement D(K1)). As another example, as illustrated by expanded view 520, the same or different aberration in the eye 404 caused a local distortion in the wavefront 410 which caused a reflected spot registering at an actual location 522 that is displaced from its expected location 524 by a displacement 526 (also denoted as displacement D(K2)).

As such, the actual locations of the reflected spots in the reflected spot pattern image 164, and their displacements from their corresponding expected locations, represent certain characteristics of the eye 404. Accordingly, at block 308 the image analysis component 162 analyzes the displacements between actual and expected locations of the reflected spots captured in the reflected spot pattern image 164 to characterize the eye 404 and provide data representative of the determined eye characterizations to the rendering component 104 as eye characterization information 156.

Any of a variety of characteristics of the eye 404 may be determined, and any of a variety of wavefront distortion analysis processes may be employed to determine such characteristics. To illustrate, as the reflected spot pattern image 164 may resemble a distorted wavefront captured by a conventional Shack-Hartmann wavefront sensor, any of a variety of well-known eye aberrometer techniques commonly applied using such conventional Shack-Hartmann wave front sensors (for example, the Complete Ophthalmic Analysis System, or COAS, technique) may similarly be adapted and employed to characterize low-order and/or high-order aberrations in the eye 404. To illustrate, as noted the displacements of the spots are directly related to the local gradient of the wavefront error (delta_x=f*[dW/dx]), and thus by spatially integrating the spot-displacement map the image analysis component 162 can recover the wavefront error W up to some constant offset (which is inconsequential). The terms in the polynomial expansion of the wavefront error correspond to the different aberrations (e.g. defocus, astigmatism, spherical, etc.). The image analysis component 164 thus can fit a polynomial to the measured wavefront error to determine the coefficients or relative weights of the different aberrations, or encode the inverse of the wavefront error in the lightfield rendering.

As another example, the image analysis component 162 may analyze the displacements in the reflected spot pattern image 164 to determine the current accommodation state of the eye 404. Similar to the aberration detection approach outlined in the paragraph above, the accommodation state is the quadratic term of the wavefront error (i.e. $W=W\_defocus*r^2$). As such, astigmatism allows for a different amount of defocus, or quadratic coefficients, along the x, y directions.

The eye characterization process represented by blocks 302, 304, 306, 308 may be triggered in any of a variety of ways. For example, the eye characterization process may be triggered once at start up to characterize the aberrations in the user's eyes, and the resulting eye characterization information may be fixed until the near-eye display system 100 is reset or until another user begins using the near-eye display system 100. In other embodiments, the eye characterization process may be repeated on a periodic basis or other basis, particularly in implementations in which the characterization includes determining the current accommodation state of the eye or other parameters of the eye that are expected to vary with some frequency.

In parallel with the eye characterization process, the rendering component 104 performs a rendering process, represented by block 310, whereby a series of lightfield frames 151 is generated for display at the display panel 118 for the left eye (and similarly, a series of lightfield frames 153 is generated for display for the right eye). For a lightfield frame to be generated and displayed, the rendering component 104 identifies the image content to be displayed to the corresponding eye of the user as a lightfield frame. In at least one embodiment, the rendering component 104 receives the pose information 152 representing data from various pose-related sensors, such as a gyroscope, accelerometer, magnetometer, Global Positioning System (GPS) sensor, and the like, and from the pose information 152 determines a pose of the apparatus 114 (e.g., HIVID) used to mount the displays 110, 112 near the user's eyes. From this pose, the CPU 136, executing the rendering program 144, can determine a corresponding current viewpoint of the subject scene or object, and from this viewpoint and graphical and spatial descriptions of the scene or object provided as rendering information 148, determine the imagery to be rendered for the pose.

In at least one embodiment, the processors 136, 138, 140 control this rendering process based on the eye characterization information generated at block 308 of the current iteration of the eye characterization process. That is, the lightfield frames are rendered by the rendering component 104 based on one or more identified characteristics of the user's eyes. To illustrate, when the eye characterization information 156 for the eye 404 includes data representing an identified aberration in the eye 404, the rendering component 104 can adjust the rendering of a lightfield frame 151 so that it compensates for the identified aberration. To illustrate, after the wavefront error (e.g. defocus, accommodation state) has been measured, the relationship between the relative shift of the elemental images that comprise the lightfield rendering can be determined by the image analysis component 164 ($dx=d\_lens*f\_lens*Phi$, where $W\_defocus=Phi/2$) and implemented by the rendering component 104 when rendering the lightfield frames. More directly, the rendering component 104 can encode the inverse of the wavefront error during rendering of the lightfield frames.

As noted above, the eye characterization information can include the current accommodation state of the eye 404. This current accommodation state reflects the current optical power of the eye's optical system, and thus is representative of current focal length of the eye 404. A mismatch between the focal plane of a lightfield image displayed to the eye 404 and this focal length can cause the human vision system to expend considerable cognitive effort to account for this mismatch or conflict, which in turn can fatigue the user. Accordingly, to minimize such accommodation/focal plane mismatches, in at least one embodiment the rendering component 104 utilizes the current accommodation state of the eye 404 as represented in the eye characterization information 156 to identify a focal length/focal plane consistent with the current accommodation state and render a next set of one or more lightfield frames 151 on the basis of the identified focal length/focal plane, and thus better matching the displayed imagery to the current focal length of the eye 404, and thereby reducing the cognitive efforts expended by the user in viewing the displayed imagery. To illustrate, there are at least two scenarios where knowing the accommodation state of the eye can facilitate lightfield rendering. First, lightfield displays have a dynamic range of accommodation states that they can represent simultaneously, given by the depth-of-field for the lenslets, $dPhi=2c/(d\_lens*f\_lens)$, where c is the minimum spot/pixel size of the system. There is a tradeoff between this depth dynamic range and the transverse spatial resolution, so the accommodation range can't be made arbitrarily large. Varifocal techniques (e.g., LC optical path difference modulators, lens-display distance modulation) can be used to shift the limited dynamic range to the plane where the user is attempting to focus. The second scenario is related to the computational bandwidth requirements for rendering lightfield images, the computation scales linearly with number of N planes that are being represented, which is problematic for mobile platforms or other systems with relatively limited computing resources. Thus, the rendering component 104 can render each lightfield frames at a single z-plane, and use the measured accommodation state to shift lightfield rendering to that plane, separately or in concert with a varifocal modality.

In some embodiments, certain aspects of the techniques described above may implemented by one or more processors of a processing system executing software. The software comprises one or more sets of executable instructions stored or otherwise tangibly embodied on a non-transitory computer readable storage medium. The software can include the instructions and certain data that, when executed by the one or more processors, manipulate the one or more processors to perform one or more aspects of the techniques described above. The non-transitory computer readable storage medium can include, for example, a magnetic or optical disk storage device, solid state storage devices such as Flash memory, a cache, random access memory (RAM) or other non-volatile memory device or devices, and the like. The executable instructions stored on the non-transitory computer readable storage medium may be in source code, assembly language code, object code, or other instruction format that is interpreted or otherwise executable by one or more processors.

A computer readable storage medium may include any storage medium, or combination of storage media, accessible by a computer system during use to provide instructions and/or data to the computer system. Such storage media can include, but is not limited to, optical media (e.g., compact disc (CD), digital versatile disc (DVD), Blu-Ray disc), magnetic media (e.g., floppy disc, magnetic tape, or magnetic hard drive), volatile memory (e.g., random access memory (RAM) or cache), non-volatile memory (e.g., read-only memory (ROM) or Flash memory), or microelectromechanical systems (MEMS)-based storage media. The computer readable storage medium may be embedded in the computing system (e.g., system RAM or ROM), fixedly attached to the computing system (e.g., a magnetic hard drive), removably attached to the computing system (e.g., an optical disc or Universal Serial Bus (USB)-based Flash memory), or coupled to the computer system via a wired or wireless network (e.g., network accessible storage (NAS)).

Note that not all of the activities or elements described above in the general description are required, that a portion of a specific activity or device may not be required, and that one or more further activities may be performed, or elements included, in addition to those described. Still further, the order in which activities are listed are not necessarily the order in which they are performed. Also, the concepts have been described with reference to specific embodiments. However, one of ordinary skill in the art appreciates that various modifications and changes can be made without departing from the scope of the present disclosure as set forth in the claims below. Accordingly, the specification and figures are to be regarded in an illustrative rather than a restrictive sense, and all such modifications are intended to be included within the scope of the present disclosure.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims. Moreover, the particular embodiments disclosed above are illustrative only, as the disclosed subject matter may be modified and practiced in different but equivalent manners apparent to those skilled in the art having the benefit of the teachings herein. No limitations are intended to the details of construction or design herein shown, other than as described in the claims below. It is therefore evident that the particular embodiments disclosed above may be altered or modified and all such variations are considered within the scope of the disclosed subject matter. Accordingly, the protection sought herein is as set forth in the claims below.

What is claimed is:

1. A near-eye display system comprising:
an array of lenslets;
a display panel facing the array of lenslets, the display panel comprising:
an array of light projecting elements, wherein each light projecting element is coaxial with an axis of a corresponding lenslet of the array of lenslets;
an array of light detecting elements; and
an array of sub-pixel elements;
a control component coupled to the display panel and configured to activate the array of light projecting elements to project a pattern of light spots toward an eye of a user and to control the array of light detecting elements to capture an image representing a reflection of the projected pattern of light spots from the eye; and
an analysis component to determine displacements between expected positions and actual positions of at least a subset of light spots in the captured image, and to characterize the eye based on the displacements.

2. The near-eye display system of claim 1, wherein the analysis component is to characterize the eye by detecting refractive aberrations in the eye based on the displacements.

3. The near-eye display system of claim 1, wherein the analysis component is to characterize the eye by detecting an accommodation state of the eye based on the displacements.

4. The near-eye display system of claim 1, further comprising:
a rendering component coupled to the display panel and configured to render a sequence of lightfield frames for display to the user via the array of sub-pixel elements.

5. The near-eye display system of claim 4, wherein the rendering component is to adjust at least one aspect of a rendering process for the sequence of lightfield frames based on the characterization of the eye.

6. The near-eye display system of claim 5, wherein:
the analysis component is to characterize the eye by detecting aberrations of the eye based on the displacements; and
the rendering component is to render the sequence of lightfield frames so as to compensate for the detected aberrations.

7. The near-eye display system of claim 5, wherein:
the analysis component is to characterize the eye by detecting a current accommodation state of the eye based on the displacements; and
the rendering component is to render the sequence of lightfield frames based on a focal plane determined from the current accommodation state.

8. The near-eye display system of claim 1, wherein:
the array of light projecting elements is configured to project the pattern of light spots as a pattern of infrared light spots.

9. The near-eye display system of claim 8, wherein the display panel comprises an array of display elements, each display element comprising at least one sub-pixel element of the array of sub-pixel elements, each display element of at least a first subset of the array of display elements further includes a light detecting element of the array of light detecting elements, and each display element of at least a second subset of the array of display elements further includes a light projecting element of the array of light projecting elements.

10. In a near-eye display system, a method comprising:
projecting a pattern of light spots from an array of light projecting elements of a display panel toward an eye of a user through a lenslet array;
capturing, via an array of light detecting elements of the display panel, an image representing a reflection of the pattern of light spots from the eye;
determining, for each light spot of at least a subset of light spots of the image, a displacement between an expected position and an actual position of the light spot in the captured image; and
determining one or more characteristics of the eye based on the displacements for the subset of the light spots.

11. The method of claim 10, wherein determining one or more characteristics of the eye comprises detecting refractive aberrations in the eye based on the displacements.

12. The method of claim 10, wherein determining one or more characteristics of the eye comprises detecting an accommodation state of the eye based on the displacements.

13. The method of claim 10, further comprising:
rendering a sequence of lightfield frames for display to the user via the display panel.

14. The method of claim 13, further comprising:
adjusting the rendering of the sequence of lightfield frames based on the characterization of the eye.

15. The method of claim 14, wherein:
determining one or more characteristics of the eye comprises detecting aberrations of the eye based on the displacements; and
adjusting the rendering comprises controlling the rendering of the sequence of lightfield frames so as to compensate for the detected aberrations.

16. The method of claim 14, wherein:
determining one or more characteristics of the eye comprises detecting a current accommodation state of the eye based on the displacements; and
adjusting the rendering comprises controlling the rendering of the sequence of lightfield frames based on a focal plane determined from the current accommodation state.

17. The method of claim 10, wherein:
projecting the pattern of light spots comprises projecting a pattern of infrared light spots.

18. A processing system comprising:
a processor; and
a memory to store data representing executable instructions, the executable instructions configured to manipulate the processor to:
  receive an image representative of a reflection of a pattern of light spots from an eye of a user;
  determine displacements between expected positions and actual positions for at least a subset of the light spots of the pattern;
  determine one or more characteristics of the eye based on the displacements; and
  render a sequence of lightfield frames for display at a near-eye display panel based on the one or more characteristics of the eye.

19. The processing system of claim 18, wherein:
the one or more characteristics of the eye comprise one or more refractive aberrations of the eye; and
the sequence of lightfield frames is rendered to compensate for the one or more refractive aberrations.

20. The processing system of claim 18, wherein:
the one or more characteristics of the eye comprise a current accommodation state of the eye; and
the sequence of lightfield frames is rendered for a focal plane that is based on the current accommodation state.

* * * * *